United States Patent
Hua

(10) Patent No.: US 11,312,959 B2
(45) Date of Patent: Apr. 26, 2022

(54) ANTISENSE OLIGONUCLEOTIDES AND THEIR USE FOR TREATING PENDRED SYNDROME

(71) Applicant: ASOcura Pharmaceuticals Suzhou Co., Ltd., Suzhou (CN)

(72) Inventor: Yimin Hua, Miami, FL (US)

(73) Assignee: ASOcura Pharmaceuticals Suzhou Co., Ltd., Suzhou (CN)

( * ) Notice: Subject to any disclaimer, the term of this patent is extended or adjusted under 35 U.S.C. 154(b) by 0 days.

(21) Appl. No.: 17/173,864

(22) Filed: Feb. 11, 2021

(65) Prior Publication Data

US 2021/0246449 A1    Aug. 12, 2021

Related U.S. Application Data

(60) Provisional application No. 62/975,337, filed on Feb. 12, 2020.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3341* (2013.01)

(58) Field of Classification Search
None
See application file for complete search history.

(56) References Cited

U.S. PATENT DOCUMENTS 4,458,066 A    7/1984    Caruthers et al.

FOREIGN PATENT DOCUMENTS

CN    104131008 A    11/2014
WO    WO2013/173637 A1    11/2013

OTHER PUBLICATIONS

Freireich, Emil J., et al., "Quantitative Comparison of Toxicity of Anticancer Agents in Mouse, Rat, Hamster, Dog, Monkey, and Man," Cancer Chemotherapy Reports, May 1966, pp. 219-244, vol. 50, No. 4.

Beaucage S.L., et al., "Deoxynucleoside Phosphoramidites—A New Class of Key Intermediates For Deoxypolynucleotide Synthesis," Tetrahedron Letters, 1981, pp. 1859-1862, vol. 22, No. 20.

Will, Cindy L., et al., "Spliceosome Structure and Function," Cold Spring Harbor Perspectives Biology, 2011, pp. 1-25.

Shimo, Takenori, et al., "Designing Effective Antisense Oligonucleotides for Exon Skipping," Camilla Bernardini (ed.), Duchenne Muscular Dystrophy: Methods and Protocols, Methods in Molecular Biology, 2018, pp. 143-155, vol. 1687.

Dowling, James J., "Eteplirsen therapy for Duchenne muscular dystrophy: skipping to the front of the line," Nature Reviews Neurology Nov. 18, 2016, pp. 1-3.

Wemeau, Jean-Louis, et al., "Pendred syndrome," Best Practice & Research Clinical Endocrinology & Metabolism 2017, pp. 213-224, vol. 31.

Son, Hae-Won, et al., "Recent Advances and Clinical Applications of Exon Inclusion for Spinal Muscular Atrophy," Methods and Protocols, Methods in Molecular Biology 2018, pp. 57-68, vol. 1828.

European Patent Office, International Search Report and Written Opinion for Application No. PCT/US2021/017595, dated May 26, 2021.

Cheng et al; Human SLC26A4 gene exon-8 PCR primer, Seq ID 36; Feb. 26, 2015; Database Geneseq [Online]; XP055795585, Database accession No. BBT80513.

Lee Byeonghyeon et al; Modified U1 snRNA and antisense oligonucleotides rescue splice mutations in SLC26A4 that cause hereditary hearing loss; Human Mutation; May 21, 2019; XP055795291; US ISSN: 1059-7794, DOI:10.1002/humu.23774; Retrieved from the Internet: URL:https://onlinelibrary.wiley.com/doi/full-xml/10.1002/humu.23774.

Ryu Nari et al; CRISPR/Cas9-mediated genome editing of splicing mutation causing congenital hearing loss; Gene; vol. 703; Mar. 18; pp. 83-90; XP085676426; ISSN: 0378-1119; DOI:10.1016/J.GENE.2019.03.020.

Minoda R et al; Potential treatments for genetic hearing loss in humans: current conundrums; Gene Therapy, Nature Publishing Group, London, GB, vol. 22, No. 8; Mar. 17, 2015; pp. 603-609; XP036971078; ISSN: 0969-7128, DOI:10.1038/GT.2015.27; retrieved on Mar. 17, 2015.

*Primary Examiner* — Tracy Vivlemore
(74) *Attorney, Agent, or Firm* — Perkins Coie LLP

(57) ABSTRACT

The present disclosure relates to the field of medicine. In particular, it relates to novel antisense oligonucleotides that prevent or reduce exon 8 skipping in the SLC26A4 gene during pre-mRNA splicing, and their use in the treatment of Pendred Syndrome.

17 Claims, 2 Drawing Sheets

Specification includes a Sequence Listing.

ANTISENSE OLIGONUCLEOTIDES AND THEIR USE FOR TREATING PENDRED SYNDROME

CROSS REFERENCES TO RELATED APPLICATIONS

This application claims priority from U.S. Provisional Patent Application No. 62/975,337, filed Feb. 12, 2020, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 10, 2021, is named 13365_0018-00304_SL.txt and is 16,709 bytes in size.

FIELD OF THE DISCLOSURE

The present invention relates to novel antisense oligonucleotides ("ASOs") that prevent or reduce exon skipping during pre-mRNA splicing, pharmaceutical compositions containing such ASOs, and their use.

BACKGROUND OF THE DISCLOSURE

Pendred syndrome is a sensorineural hearing loss disorder. It is one of the most frequent causes of syndromic deafness, accounting for about 4-10% of all hereditary deafness cases. Patients with Pendred syndrome have a malformed inner ear, including an enlarged vestibular aqueduct. Sometimes a Mondini cochlea can also develop, where the cochlear and intermediate septum are entirely or partially replaced by a fluid filled cavity. While the hearing loss caused by the syndrome is typically congenital, some rare cases develop later in childhood. Some patients (50-83%) will additionally present with a goiter, although this is variable as it depends on other factors such as nutritional intake. Wemeau & Kopp, (2017) *Best Prac. & Res. Clin. Endocrinology & Metabolism* 31, 213-224.

Early treatment of Pendred syndrome is crucial for congenital cases in order to ensure language acquisition and communication skills. Current options for Pendred syndrome treatment include audiological support devices such as hearing aids, which can help mild hearing impairments. However, in patients with severe deafness, a cochlear implant may be recommended. The implantation process may cause a leak of cerebro-spinal fluid in patients with a Mondini cochlea. Wemeau & Kopp, (2017) *Best Prac. & Res. Clin. Endocrinology & Metabolism* 31, 213-224. Currently, there are no drugs available to treat Pendred syndrome, and no treatment options directed to the underlying genetic cause of Pendred syndrome.

Pendred syndrome is an autosomal recessive disorder characterized by a biallelic mutation in the SLC26A4 gene that encodes pendrin. Pendrin is a multifunctional anion exchanger protein expressed in the inner ear and thyroid. With an affinity for chloride, iodide, and other anions, pendrin maintains the composition and potential of the endolymph by facilitating the exchange of chloride and bicarbonate in the inner ear. Wemeau & Kopp, (2017) *Best Prac. & Res. Clin. Endocrinology & Metabolism* 31, 213-224. A mutation in the SLC26A4 gene (c.919-2A>G) causes exon 8 skipping during processing of SLC26A4 pre-mRNA. The mutation, also known as IVS7-2A>G, is one of the most common mutations in East Asian populations with hearing loss.

In eukaryotic genes containing coding (exons) and non-coding (intron) sequences, the noncoding introns are excised from the pre-mRNA transcript and the coding exons are spliced together to form mRNA. If an intron is left in the final mRNA transcript or an exon is left out, the mRNA reading frame may be disrupted during translation of the mRNA. This may result in a non-functional polypeptide sequence or a premature stop codon. The splicing process is further complicated by alternative splicing, where the same pre-mRNA sequence can be spliced into different exon combinations to form multiple mRNA sequences.

Splicing of pre-mRNA is an intricate process involving a multi-megadalton ribonucleoprotein complex called the spliceosome. The spliceosome recognizes specific sequences in pre-mRNA to precisely excise introns and ligate exons. The spliceosome catalyzes intron excision in two transesterification reactions using three conserved RNA sequences. These RNA sequences are the 5' splice site, 3' splice site, and the branch site. Will & Luhrmann, (2011) *Cold Spring Harb. Perspect. Biol.* 3, a003707.

Splicing begins with the 2' OH group of the branch site binding to the 5' splice site via a nucleophilic attack, causing cleavage of the 5' exon at the 5' splice site and forming a lariat. Then the 3' OH group of the 5' exon attacks the 3' exon at the 3' splice site, ligating the 5' and 3' exons and cleaving the intron lariat. Will & Luhrmann, (2011) *Cold Spring Harb. Perspect. Biol.* 3, a003707. Because the splicing process is entirely dependent on spliceosome recognition sites, 5' and 3' splice sites, and the branch site, a mutation in any one of these sites can disrupt the splicing process.

In Pendred syndrome, the (c.919-2A>G) mutation in SLC26A4 affects the splicing process of the SLC26A4 pre-mRNA, causing exon 8 skipping. The incorrect removal of exon 8 from the final mRNA transcript causes a disruption of the reading frame during translation, resulting in a truncated and dysfunctional pendrin peptide. Wemeau & Kopp, (2017) *Best Prac. & Res. Clin. Endocrinology & Metabolism* 31, 213-224.

ASOs are polynucleotides designed to bind with specificity to a target nucleotide sequence, thereby affecting one or more aspects of gene expression, such as, transcription, splicing, stability, and/or translation. ASOs may be directed to either RNA or DNA. ASOs directed to RNA can bind to target mRNA sequences, effecting mRNA stability or translation at the ribosome.

ASOs that bind to target sequences in pre-mRNA transcripts can affect the splicing process. In some cases, ASOs may be used to induce exon skipping during pre-mRNA splicing. For example, Duchenne Muscular Dystrophy (DMD) is caused by a mutation that alters the reading frame of dystrophin mRNA during translation, resulting in a premature stop codon and truncated dystrophin protein. ASOs may be utilized to correct the reading frame by inducing skipping of an exon during splicing. Removing an exon of the correct number of base pairs results in a shorter mRNA transcript, but the reading frame may be corrected. Because dystrophin RNA consists of 79 exons, skipping one or several exons during splicing still results in a partly functional protein. Shimo et al., (2015) *Duchenne Muscular Dystrophy* 143-155. The FDA approved an exon-skipping drug called Exondys 51 (eteplirsen) for treatment of DMD in 2016. Dowling, (2016) *Nature Review Neurology* 12, 675-676.

In other cases, ASOs may be used to prevent or reduce exon skipping during pre-mRNA splicing. As an example, the ASO drug nusinersen (Spinraza®) reduces exon 7 skipping during splicing of the SMN2 gene to treat spinal muscular atrophy. Son & Yokota, (2018) *Exon Skipping & Inclusion Therapies,* 57-68. There remains a need, however, for ASOs that successfully prevent or reduce exon 8 skipping during pre-mRNA splicing of SLC26A4 and for their use in treating related conditions such as Pendred syndrome.

SUMMARY OF THE DISCLOSURE

The present invention relates to ASOs, methods of using such ASOs to prevent or reduce exon skipping during pre-mRNA splicing, pharmaceutical compositions that comprise such ASOs, and methods of using such compositions to treat hearing loss in Pendred syndrome.

In an embodiment, the present invention provides an ASO of 10-30 nucleotides in length comprising all or a portion of SEQ ID NO:1.

In an embodiment, the present invention provides an ASO, wherein the ASO is:

```
a. HUA0003-1027
                                   (SEQ ID NO: 2)
   (5'-tagtactaagaggaacac-3');

b. HUA0003-1029
                                   (SEQ ID NO: 3)
   (5'-attagtactaagaggaacac-3');

c. HUA0003-1030
                                   (SEQ ID NO: 4)
   (5'-tattagtactaagaggaacac-3');

d. HUA0003-1031
                                   (SEQ ID NO: 5)
   (5'-gtattagtactaagaggaacac-3');

e. HUA0003-1032
                                   (SEQ ID NO: 6)
   (5'-tgtattagtactaagaggaacac-3');

f. HUA0003-0930
                                   (SEQ ID NO: 7)
   (5'-tattagtactaagaggaacacc-3');

g. HUA0003-0929
                                   (SEQ ID NO: 8)
   (5'-attagtactaagaggaacacc-3');

h. HUA0003-0928
                                   (SEQ ID NO: 9)
   (5'-ttagtactaagaggaacacc-3');
   or i. HUA0003-0931
                                   (SEQ ID NO: 10)
   (5'-gtattagtactaagaggaacacc-3').
```

In an embodiment, the present invention provides an ASO mentioned above comprising a non-natural backbone.

In an embodiment, the present invention provides an ASO mentioned above comprising modified sugar moieties.

In an embodiment, the present invention provides an ASO mentioned above comprising 2'-O-methoxyethyl ribose moieties.

In an embodiment, the present invention provides an ASO mentioned above comprising modified phosphates.

In an embodiment, the present invention provides an ASO mentioned above comprising phosphorothioates.

In an embodiment, the present invention provides an ASO mentioned above comprising modified nitrogenous bases.

In an embodiment, the present invention provides an ASO mentioned above comprising 5-methylcytosine bases.

In an embodiment, the present invention provides an ASO mentioned above further comprising a pharmaceutically acceptable carrier or excipient.

In an embodiment, the present invention provides a method of preventing or reducing exon 8 skipping in the SLC26A4 gene during pre-mRNA splicing, comprising introducing a nucleic acid molecule into a cell, wherein the nucleic acid molecule is an ASO comprising all or a portion of SEQ ID NO:1, wherein the ASO hybridizes to an intron 8 target region of the SLC26A4 gene, and wherein the ASO prevents or reduces exon 8 skipping during pre-mRNA splicing of the SLC26A4 gene.

In an embodiment, the present invention provides a method of preventing or reducing exon 8 skipping in the SLC26A4 gene during pre-mRNA splicing mentioned above, wherein the ASO is:

```
a. HUA0003-1027
                                   (SEQ ID NO: 2)
   (5'-tagtactaagaggaacac-3');

b. HUA0003-1029
                                   (SEQ ID NO: 3)
   (5'-attagtactaagaggaacac-3');

c. HUA0003-1030
                                   (SEQ ID NO: 4)
   (5'-tattagtactaagaggaacac-3');

d. HUA0003-1031
                                   (SEQ ID NO: 5)
   (5'-gtattagtactaagaggaacac-3');

e. HUA0003-1032
                                   (SEQ ID NO: 6)
   (5'-tgtattagtactaagaggaacac-3');

f. HUA0003-0930
                                   (SEQ ID NO: 7)
   (5'-tattagtactaagaggaacacc-3');

g. HUA0003-0929
                                   (SEQ ID NO: 8)
   (5'-attagtactaagaggaacacc-3');

h. HUA0003-0928
                                   (SEQ ID NO: 9)
   (5'-ttagtactaagaggaacacc-3');
   or i. HUA0003-0931
                                   (SEQ ID NO: 10)
   (5'-gtattagtactaagaggaacacc-3').
```

In an embodiment, the present invention provides a method of preventing or reducing exon 8 skipping in the SLC26A4 gene during pre-mRNA splicing mentioned above, wherein the cell is an animal cell.

In an embodiment, the present invention provides a method of preventing or reducing exon 8 skipping in the SLC26A4 gene during pre-mRNA splicing mentioned above, wherein the cell is a human cell.

In an embodiment, the present invention provides a method of preventing or reducing exon 8 skipping in the SLC26A4 gene during pre-mRNA splicing mentioned above, wherein the nucleic acid molecule is introduced into a cell by way of an expression vector.

In an embodiment, the present invention provides a method of preventing or reducing exon 8 skipping in the SLC26A4 gene during pre-mRNA splicing mentioned above, wherein the expression vector is a pCI-neo expression vector.

In an embodiment, the present invention provides a method of treating hearing loss in a subject having Pendred syndrome comprising administering a therapeutically effective amount of an ASO comprising all or a portion of SEQ ID NO:1.

In an embodiment, the present invention provides a method of treating hearing loss in a subject having Pendred syndrome mentioned above, wherein the ASO administered is:

a. HUA0003-1027
  (SEQ ID NO: 2)
  (5'-tagtactaagaggaacac-3');

b. HUA0003-1029
  (SEQ ID NO: 3)
  (5'-attagtactaagaggaacac-3');

c. HUA0003-1030
  (SEQ ID NO: 4)
  (5'-tattagtactaagaggaacac-3');

d. HUA0003-1031
  (SEQ ID NO: 5)
  (5'-gtattagtactaagaggaacac-3');

e. HUA0003-1032
  (SEQ ID NO: 6)
  (5'-tgtattagtactaagaggaacac-3');

f. HUA0003-0930
  (SEQ ID NO: 7)
  (5'-tattagtactaagaggaacacc-3');

g. HUA0003-0929
  (SEQ ID NO: 8)
  (5'-attagtactaagaggaacacc-3');

h. HUA0003-0928
  (SEQ ID NO: 9)
  (5'-ttagtactaagaggaacacc-3');
or i. HUA0003-0931
  (SEQ ID NO: 10)
  (5'-gtattagtactaagaggaacacc-3').

In an embodiment, the present invention provides a method of treating hearing loss in a subject having Pendred syndrome mentioned above, wherein the ASO is administered via parenteral administration.

In an embodiment, the present invention provides a compound for use in a method of preventing or reducing exon 8 skipping in the SLC26A4 gene during pre-mRNA splicing, comprising introducing a nucleic acid molecule into a cell, wherein the nucleic acid molecule is an ASO comprising all or a portion of SEQ ID NO:1.

In an embodiment, the present invention provides a compound for use in a method of preventing or reducing exon 8 skipping in the SLC26A4 gene during pre-mRNA splicing mentioned above, wherein the ASO is:

a. HUA0003-1027
  (SEQ ID NO: 2)
  (5'-tagtactaagaggaacac-3');

b. HUA0003-1029
  (SEQ ID NO: 3)
  (5'-attagtactaagaggaacac-3');

c. HUA0003-1030
  (SEQ ID NO: 4)
  (5'-tattagtactaagaggaacac-3');

d. HUA0003-1031
  (SEQ ID NO: 5)
  (5'-gtattagtactaagaggaacac-3');

e. HUA0003-1032
  (SEQ ID NO: 6)
  (5'-tgtattagtactaagaggaacac-3');

f. HUA0003-0930
  (SEQ ID NO: 7)
  (5'-tattagtactaagaggaacacc-3');

g. HUA0003-0929
  (SEQ ID NO: 8)
  (5'-attagtactaagaggaacacc-3');

h. HUA0003-0928
  (SEQ ID NO: 9)
  (5'-ttagtactaagaggaacacc-3');
or i. HUA0003-0931
  (SEQ ID NO: 10)
  (5'-gtattagtactaagaggaacacc-3').

In an embodiment, the present invention provides a compound for use in a method of preventing or reducing exon 8 skipping in the SLC26A4 gene during pre-mRNA splicing mentioned above, wherein the cell is an animal cell.

In an embodiment, the present invention provides a compound for use in a method of preventing or reducing exon 8 skipping in the SLC26A4 gene during pre-mRNA splicing mentioned above, wherein the cell is a human cell.

In an embodiment, the present invention provides a compound for use in a method of preventing or reducing exon 8 skipping in the SLC26A4 gene during pre-mRNA splicing mentioned above, wherein the nucleic acid molecule is introduced into a cell via an expression vector.

In an embodiment, the present invention provides a compound for use in a method of preventing or reducing exon 8 skipping in the SLC26A4 gene during pre-mRNA splicing mentioned above, wherein the expression vector is a pCI-neo expression vector.

In an embodiment, the present invention provides a compound for use in a method of treating hearing loss in a subject having Pendred syndrome comprising administering a therapeutically effective amount of an ASO comprising all or a portion of SEQ ID NO: 1.

In an embodiment, the present invention provides a compound for use in a method of treating hearing loss in a subject having Pendred syndrome mentioned above, wherein the ASO is:

a. HUA0003-1027
  (SEQ ID NO: 2)
  (5'-tagtactaagaggaacac-3');

b. HUA0003-1029
  (SEQ ID NO: 3)
  (5'-attagtactaagaggaacac-3');

c. HUA0003-1030
  (SEQ ID NO: 4)
  (5'-tattagtactaagaggaacac-3');

d. HUA0003-1031
  (SEQ ID NO: 5)
  (5'-gtattagtactaagaggaacac-3');

e. HUA0003-1032
  (SEQ ID NO: 6)
  (5'-tgtattagtactaagaggaacac-3');

-continued f. HUA0003-0930
(SEQ ID NO: 7)
(5'-tattagtactaagaggaacacc-3');

g. HUA0003-0929
(SEQ ID NO: 8)
(5'-attagtactaagaggaacacc-3');

h. HUA0003-0928
(SEQ ID NO: 9)
(5'-ttagtactaagaggaacacc-3');
or i. HUA0003-0931
(SEQ ID NO: 10)
(5'-gtattagtactaagaggaacacc-3').

In an embodiment, the present invention provides a compound for use in a method of treating hearing loss in a subject having Pendred syndrome mentioned above, wherein the ASO is administered via parenteral administration.

DETAILED DESCRIPTION

Definitions

Figure 1:
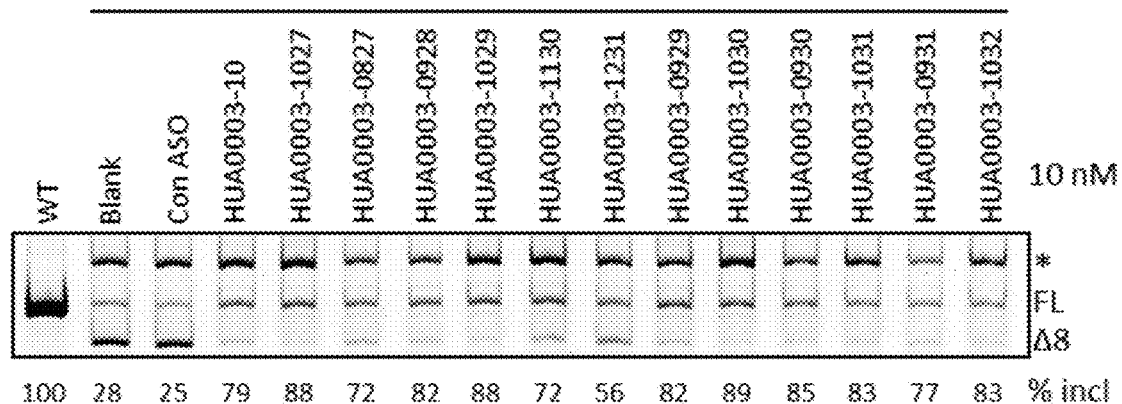
FIG. 1 shows the identification of ASOs that promote exon 8 inclusion for an SLC26A4 minigene c.919-2A>G mutant. The percentage of exon 8 inclusion in untreated cells (Blank) is ~30%. Percent inclusion in cells treated with 10 nM control ASO (Con ASO) is ~26%. FL: full-length transcript, *: intron 7-retention transcript, Δ8: exon 8-skipped transcript.

The term "oligonucleotide" is used herein to refer to a nucleotide sequence comprising at least ten DNA or RNA nucleotides.

The term "antisense oligonucleotide," abbreviated as "ASO," is used herein to refer to a nucleotide sequence comprising an antisense sequence that is sufficiently complementary to a target nucleotide sequence in order to form a stable double stranded hybrid with the target nucleotide sequence. In some embodiments, the target nucleotide sequence is an RNA nucleotide sequence.

The term "nucleobase" is used herein to refer to a nitrogenous base that is a component of a nucleoside. Example nucleobases include, but are not limited to, adenine, guanine, thymine, cytosine, and uracil.

The term "nucleoside" is used herein to refer to a nucleobase covalently linked to a sugar. Examples of naturally occurring and non-natural nucleosides are described below.

The term "nucleotide" is used herein to refer to a nucleoside covalently linked to a phosphate group. Examples of naturally occurring and non-natural nucleotides are described below.

The term "non-natural" is used herein to refer to one or more nucleotide subunits having at least one modification selected from (i) a modified internucleotide linkage, e.g., an internucleotide linkage other than the standard phosphodiester linkage found in naturally-occurring oligonucleotides, (ii) modified sugar moieties, e.g., moieties other than ribose or deoxyribose moieties found in naturally occurring oligonucleotides, (iii) modified nitrogenous bases, e.g., bases other than those found in naturally occurring oligonucleotides, or (iv) a combination of the foregoing.

The term "morpholino" is used herein to refer to a nucleobase that contains a morpholinyl ring instead of a ribose.

The term "complementary" is used herein to describe when the corresponding positions of at least two nucleotide sequences are occupied by nucleotides which can hydrogen bond with each other.

The term "hybridize" is used herein to describe the binding of two complementary nucleotide sequences, forming one double stranded molecule. When a sufficient number of corresponding nucleotides in two sequences can hydrogen bond with each other in order, i.e., they are sufficiently complementary, they may form a stable hybrid. It is understood in the art that 100% complementarity is not necessary for an ASO to hybridize with a target sequence.

The term "sufficient complementarity" is used herein to indicate a level of complementarity sufficient to permit an ASO to specifically bind to its target sequence and form a stable hybrid. In one embodiment, the complementarity of the ASO and the target sequence is at least 99%, or 98%, or 97%, or 96%, or 95%, or 94%, or 93%, or 92%, or 91%, or 90%, or 89%, or 88%, or 87%, or 86%, or 85%, or 84%, or 83%, or 82%, or 81%, or 80%, or 79%, or 78%, or 77%, or 76%, or 75%, or 74%, or 73%, or 72%, 71%, or 70%.

The terms "target region" and "target sequence" are used interchangeably herein to designate a nucleotide sequence to which an ASO will hybridize under physiological conditions. It is not necessary for the ASO and the target region to be 100% complementary, so long as there is sufficient complementarity for the ASO to hybridize to the target sequence and form a stable hybrid. The ASO may hybridize to all or a portion of the target sequence.

The terms "treat," "treating," or "treatment" are used herein to refer to ameliorating a disease or disorder (i.e., slowing or arresting or reducing the development of the disease or at least one of the clinical symptoms thereof). The terms also refer to alleviating or ameliorating at least one physical parameter including those which may not be discernible by the patient. The terms also refer to modulating the disease or disorder, either physically (e.g., through stabilization of a discernible symptom), physiologically, (e.g., through stabilization of a physical parameter), or both. The terms also refer to preventing or delaying the onset or development or progression of the disease or disorder The term "therapeutically effective amount" is used herein to refer to the amount of a therapeutic agent or composition effective in prevention or treatment of a disorder or disease. In one embodiment, this includes an amount of a therapeutic agent or composition effective in the prevention or treatment of Pendred syndrome.

The term "pharmaceutically acceptable" is used herein to refer to a molecular entity or composition that is pharmaceutically useful and not biologically or otherwise undesirable.

The term "carrier" is used herein to refer to a diluent, adjuvant, excipient, or vehicle with which the compound is administered.

The term "excipient" as used herein refers to any ingredient in a pharmaceutical composition other than the active ingredient.

Unless otherwise defined, all other scientific and technical terms have the same meaning as commonly understood to one of ordinary skill in the art. Such scientific and technical terms are explained in the literature, for example: J. Sambrook, E. F. Fritsch, and T Maniatis, 1989, *Molecular Cloning: A Laboratory Manual*, Second Edition, Books 1-3, Cold Spring Harbor Laboratory Press; Martin, 1990, *Remington's Pharmaceutical Sciences,* 18th Edition, Mack Publishing Co; Glover, 1985, *DNA Cloning: A Practical Approach*, Volumes I and II, MRL Press, Ltd.; and Ausubel, F., Brent, R., Kingston, R. E., Moore, D. D., Seidman, J. G., Smith, J. A., Struhl, K., 2002, *Current Protocols in Molecular Biology*, Greene Publishing Associates/Wiley Intersciences.

Antisense Oligonucleotides

In one embodiment, disclosed herein are ASOs directed to a target sequence in the SLC26A4 pre-mRNA. Some embodiments are directed to ASOs directed to all or a portion of a 25-nucleotide target sequence of intron 8 in the SLC26A4 pre-mRNA (Table 1, "25-Nt Sequence of Interest"). This target sequence is from position 8 to position 32 of intron 8 in the SLC26A4 gene. This intron 8 target sequence is involved in exon 8 skipping that occurs in mutant (c.919-2A>G) SLC26A4 whereby pre-mRNA containing the mutation is incorrectly spliced, removing exon 8 from the final transcript.

In another embodiment, ASOs that are directed to the 25-nt target sequence are sufficiently complimentary to the target sequence to form a stable hybrid and are 10-30 nucleotides in length. These ASOs are sufficiently complimentary to all or a portion of the 25-nt target sequence.

In some embodiments, the ASOs have the specific sequences disclosed in Table 3. Those specific ASOs are also illustrated in the Example. However, these specific ASOs are disclosed for illustrative purposes only and are not to limit the scope of the invention in any way.

In some embodiments, at least some nucleobases of the ASOs will replace thymine with uracil, or uracil with thymine. In some embodiments, at least some nucleosides of the ASOs will replace deoxyribose with ribose, or ribose with deoxyribose.

Nucleotide Modifications

In another embodiment, the disclosed ASOs comprise one or more nucleotides that are chemically modified in one or more ways known to those of skill in the art. Nucleotide modifications include, for example, modified nitrogenous bases, sugar moieties, and phosphates. Such modifications are preferable at least in their ability to resist nuclease degradation.

Specific examples of chemically modified ASOs useful in this invention include ASOs containing modified phosphate backbones or non-natural inter-nucleoside linkages. ASOs having modified backbones include those that retain a phosphorus atom in the backbone and those that do not have a phosphorus atom in the backbone.

In other embodiments, both the sugar and the internucleoside linkage, i.e., the backbone, of the nucleotide units in the ASO are replaced with novel groups. The base units are maintained for hybridization with an appropriate nucleic acid target compound. For example, the ASO may be a peptide nucleic acid (PNA). In PNA compounds, the sugar-backbone of an oligonucleotide is replaced with an amide containing backbone, for example, an aminoethylglycine backbone. The nucleo-bases are retained and are bound directly or indirectly to aza nitrogen atoms of the amide portion of the backbone.

Modified ASOs may also contain one or more substituted sugar moieties, for example, one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylaminooxyethoxy; and -dimethylaminoethoxyethoxy. The sugar moiety can be a pyranose or derivative thereof, or a deoxypyranose or derivative thereof, or a ribose or derivative thereof, or a deoxyribose or derivative of. In one embodiment, the substituted sugar moiety is a 2'-O-methoxyethyl moiety.

Modified ASOs may also contain one or more nucleobase (often referred to in the art simply as "base") modifications or substitutions, for example, 5-substituted pyrimidines, 6-azapyrimidines and N-2, N-6 and O-6 substituted purines, including 2-aminopropyladenine, 5-propynyluracil and 5-propynylcytosine. Certain nucleobases are particularly useful for increasing the binding affinity of the oligomeric compounds of the invention. 5-methylcytosine substitutions have been shown to increase nucleic acid duplex stability by 0.6-1.2° C.

Another modification of the ASOs of the invention involves chemically linking to the ASO one or more moieties or conjugates that enhance the activity, cellular distribution or cellular uptake of the ASO. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Another modification to the ASO includes morpholino-based ASOs. Morpholino-based oligomers refer to an oligomer comprising morpholino subunits supporting a nucleobase and, instead of a ribose, contains a morpholinyl ring. Exemplary internucleotide linkages include, for example, phosphoramidate or phosphorodiamidate internucleotide linkages joining the morpholinyl ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based ASOs (including modified ASOs) are detailed, for example, in U.S. Pat. Nos. 5,698,685; 5,217,866; 5,142,047; 5,034,506; 5,166,315; 5,185,444; 5,521,063; 5,506,337, which are hereby incorporated by reference in their entirety.

Within the ASO structure, the phosphate groups are commonly referred to as forming the "internucleotide linkages" of the ASO. The naturally occurring internucleotide linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. A "phosphorotriamidate" group (or a phosphoric acid triamide group) comprises phosphorus having one attached oxygen atom and three attached nitrogen atoms. In the uncharged or the cationic internucleotide linkages of the morpholino-based ASOs described herein, one nitrogen is always pendant to the linkage chain. The second nitrogen, in a phosphorodiamidate linkage, is typically the ring nitrogen in a morpholino ring structure.

It is not necessary for all positions in a given ASO to be uniformly modified, and in fact more than one of the aforementioned modifications may be incorporated in a single nucleoside within an ASO. ASOs may contain at least one region wherein the ASO is modified to confer upon them increased resistance to nuclease degradation, increased cellular uptake, and/or an additional region for increased binding affinity for the target nucleic acid.

Manufacturing Antisense Oligonucleotides

The antisense molecules used in accordance with this invention may be made through well-known techniques of solid phase synthesis. Equipment for such synthesis is available from several sources including, for example, Applied Biosystems (Foster City, Calif.). One method for synthesizing oligonucleotides on a modified solid support is described in U.S. Pat. No. 4,458,066.

Any other means for such synthesis known in the art may additionally or alternatively be employed. It is well known to use similar techniques to prepare oligonucleotides such as the phosphorothioates and alkylated derivatives. In one such automated embodiment, diethyl-phosphoramidites are used as starting materials and may be synthesized as described by Beaucage, et al., (1981) *Tetrahedron Letters,* 22:1859-1862.

The ASOs of the invention are synthesized in vitro and do not include antisense compositions of biological origin. The ASOs of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Methods of Preventing or Reducing Exon 8 Skipping During pre-mRNA Splicing

The ASOs described above can be used to prevent or reduce exon 8 skipping during processing of pre-mRNA transcribed from the mutant (c.919-2A>G) SLC26A4 gene.

Accordingly, in one embodiment, there is disclosed methods of using ASOs to prevent or reduce exon 8 skipping in mutant (c.919-2A>G) SLC26A4 gene during pre-mRNA splicing by introducing an ASO into a cell, wherein the ASO comprises all or a portion of SEQ ID NO:1, wherein the ASO hybridizes to an intron 8 target region of the SLC26A4 gene, and wherein the ASO prevents or reduces exon 8 skipping during pre-mRNA splicing of the SLC26A4 gene. In another embodiment, the ASO administered to prevent or reduce exon 8 skipping during pre-mRNA splicing comprises one of SEQ ID NOS:2-10.

In one embodiment, the ASO is administered by itself, as a so-called "naked" ASO. The naked ASO is synthesized in vitro. Naked ASOs can be introduced into a cell to directly hybridize to an intron 8 target region of the SLC26A4 gene to prevent or reduce exon 8 skipping during pre-mRNA splicing.

In another embodiment, the ASO is administered in the form of an expression vector, wherein the expression vector encodes an RNA transcript comprising the sequence of said ASO according to the invention. When placed under conditions conducive to expression of the encoded ASO, the expression vector can express the encoded ASO, which can hybridize to an intron 8 target region of the SLC26A4 gene to prevent or reduce exon 8 skipping during pre-mRNA splicing. The expression vector can be a viral or non-viral vector. In one embodiment, there is provided a plasmid-based expression vector comprising an expression cassette or a transcription cassette that drives expression or transcription of an ASO for redirecting splicing according to the invention.

A cell can be provided with an ASO for redirecting splicing according to the invention by plasmid-derived ASO expression or viral expression provided by cytolomegalovirus-, adenovirus- or adeno-associated virus-based vectors. Expression may be driven by an RNA polymerase II promoter (Pol II) such as a U7 RNA promoter or an RNA polymerase III (Pol III) promoter, such as a U6 RNA promoter. In one embodiment, the delivery vehicle is a vector such as a pCI-neo vector and the like. Also, plasmids and artificial chromosomes are usable for targeted homologous recombination and integration in the human genome of cells may be suitably applied for delivery of an ASO for redirecting splicing according to the invention.

Methods of introducing "naked" ASOs or expression vectors encoding ASOs into a cell are well known in the art. An ASO or expression vector encoding an ASO can be introduced by transfection using known transfection agents. In one embodiment, the use of an excipient or transfection agent aids in delivery of the ASO or expression vector encoding the ASO as defined herein to a cell and/or into a cell. In another embodiment, excipients or transfection agents are capable of forming complexes, nanoparticles, micelles, vesicles and/or liposomes that deliver each ASO or expression vector encoding each ASO as defined herein, complexed or trapped in a vesicle or liposome through a cell membrane. Many of these excipients are known in the art. Suitable excipients or transfection agents include, but are not limited to, LipofectAMINE™ 2000 (Invitrogen), polyethylenimine (PEI; ExGen500 (MBI Fermentas)), or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each ASO or expression vector encoding each ASO as defined herein to a cell. Such excipients have been shown to efficiently deliver an oligonucleotide such as ASOs to a wide variety of cultured cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Therapeutic Methods

The ASOs described above can be used to treat hearing loss in a subject having Pendred syndrome.

Accordingly, in one embodiment, the present invention also describes methods of using ASOs to treat hearing loss in a subject having Pendred syndrome comprising administering a therapeutically effective amount of all or a portion of SEQ ID NO:1.

In another embodiment, the ASO administered to treat hearing loss in a subject having Pendred syndrome comprises one of SEQ ID NOS:2-10.

The amount of ASO administered in a pharmaceutical composition may be dependent on the subject being treated, the subject's weight, the manner of administration and the judgment of the prescribing physician. For example, a dosing schedule may involve the daily or semi-daily administration of the pharmaceutical composition at a perceived dosage of about 1 µg to about 1000 mg. In another embodiment, intermittent administration, such as on a monthly or yearly basis, of a dose of the pharmaceutical composition may be employed. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966).

The ASOs described above may be administered in a pharmaceutical composition comprising therapeutically effective amounts of an ASO together with pharmaceutically acceptable excipients, diluents, preservatives, solubilizers, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. The compositions may be prepared in liquid form, or may be in dried powder, such as lyophilised form.

Administration

A pharmaceutical composition comprising an ASO and a pharmaceutically acceptable carrier or excipient may be prepared for administration according to techniques well known in the pharmaceutical industry. Such techniques include, but are not limited to, combining the ASO with the carrier and/or excipient(s) into association in a unit dosage form.

Compositions suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one embodiment of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one embodiment of the present disclosure, which may be optionally combined with one or more accessory ingredients. Compressed tablets may be prepared by compressing, in a suitable machine, at least one embodiment of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one embodiment of the present disclosure is moistened with an inert liquid diluent.

Formulations suitable for buccal (sub-lingual) administration include lozenges comprising at least one embodiment of the present disclosure in a flavored base, usually sucrose and acacia or tragacanth, and pastilles comprising the at least one compound in an inert base such as gelatin and glycerin or sucrose and acacia.

Formulations suitable for parenteral administration comprise sterile aqueous preparations of at least one embodiment of the present disclosure, which are approximately isotonic with the blood of the intended recipient. These preparations are administered intravenously, although administration may also be affected by means of subcutaneous, intramuscular, intraperitoneal, intracerebroventricular, or intradermal injection. Such preparations may conveniently be prepared by admixing at least one embodiment described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one embodiment as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The ASO is generally present at a concentration of from about 0.1% to about 15% w/w of the composition, for example, from about 0.5 to about 2%.

Example

The following Example serves to more fully describe the invention. It is meant for illustrative purposes and is not meant to limit the invention in any way.

Materials and Methods

ASOs modified with 2'-O-methoxyethyl (MOE) ribose, a phosphorothioate (PS) backbone, and containing 5-methylcytosines in place of all cytosines were purchased from Biosyntech (Suzhou, China) and dissolved in DEPC-treated water with a stock solution at 20 μM. A human SLC26A4 minigene c.919-2A>G mutant (1212 bp) comprising of the 153-nt exon 7, the 100-nt intron 7, the 83-nt exon 8, a shortened 701-nt intron 8 (382+6+313), the 148-nt exon 9, and the first 27-nt sequence of intron 9, was constructed in pCI-neo vector via two steps. First, a 718-nt genomic DNA fragment (from exon 7 to the first 382-bp sequence of intron 8) was cloned in the vector at restriction sites XhoI and XbaI and then a 488-bp genomic DNA fragment (from the last 313-bp sequence of intron 8 to the first 27-nt sequence of intron 9) was cloned at restriction sites XbaI and NotI.

Each ASO was co-transfected transiently with the SLC26A4 minigene mutant into HEK293 cells using LipofectAMINE™ 2000. 48 hr post transfection, cells were collected and total RNA isolated. Transcripts were amplified with semi-quantitative RT-PCR using Cy5-conjugated primers. Cy5-labeled PCR products were separated with 6% native polyacrylamide gels, followed by imaging with G:BOX Chem XL or FluorChem M system. The percentage of exon 8 inclusion (% incl) was calculated with Image J software. % incl=full-length transcript/(full-length transcript+exon 8 skipped transcript.

Results

Human SLC26A4 exon 8 with the 2A>G mutation

Exon 8 (uppercase), flanking intron sequences(lowercase), and c.919-2A>G mutation (ĝ) are:

```
                                            (SEQ ID NO: 40)
<gtaagtagaatatgtagttagaaagttcagc attatttggttgacaaacaaggaattattaaa accaatggagtttttaacatcttttgttttat ttcĝgACGATAATTGCTACTGCCATTTCATAT

GGAGCCAACCTGGAAAAAAATTACAATGCTGG

CATTGTTAAATCCATCCCAAGGGGgtgagtgt ggtgttcctcttagtactaatacattaagtca gtaagtcagtctttttttatttaaataaaacct tttattacaagcttca.>
```

A large number of ASOs targeting a sequence within the 81 nucleotides of the 3' end of exon 8 and the 74 nucleotides at the 5' end of intron 8 were designed and screened using the above minigene system. Multiple ASOs promoted exon 8 splicing in cultured cells (FIG. 1). ASO sequences and splicing data are shown in Tables 1-2. We identified a 25-nt stretch (underlined above) in intron 8 as an ideal ASO target. The sequence (5'-tggtgttcctcttagtactaataca-3' (SEQ ID NO:41)) starts from position 8 of intron 8 to position 32 of the intron.

TABLE 1

| ASO name | Sequence (5' to 3') | nt | Target Sequence name | Target (5' to 3') | >58% |
| --- | --- | --- | --- | --- | --- |
| HUA0003-01 (SEQ ID NO: 11) | GCAGTAGCAATTATC | 15 | SEQ ID NO: 42 | GATAATTGCTACTGC | No |
| HUA0003-02 (SEQ ID NO: 12) | ATATGAAATGGCAGT | 15 | SEQ ID NO: 43 | ACTGCCATTTCATAT | No |
| HUA0003-03 (SEQ ID NO: 13) | GGTTGGCTCCATATG | 15 | SEQ ID NO: 44 | CATATGGAGCCAACC | No |
| HUA0003-04 (SEQ ID NO: 14) | TTTTTTTCCAGGTTG | 15 | SEQ ID NO: 45 | CAACCTGGAAAAAAA | No |
| HUA0003-05 (SEQ ID NO: 15) | AGCATTGTAATTTTT | 15 | SEQ ID NO: 46 | AAAAATTACAATGCT | No |
| HUA0003-06 (SEQ ID NO: 16) | TAACAATGCCAGCAT | 15 | SEQ ID NO: 47 | ATGCTGGCATTGTTA | No |

TABLE 1-continued

| ASO name | Sequence (5' to 3') | nt | Target Sequence name | Target (5' to 3') | >58% |
|---|---|---|---|---|---|
| HUA0003-07 (SEQ ID NO: 17) | GGGATGGATTTAACA | 15 | SEQ ID NO: 48 | TGTTAAATCCATCCC | No |
| HUA0003-08 (SEQ ID NO: 18) | TCACCCCCTTGGGAT | 15 | SEQ ID NO: 49 | ATCCCAAGGGGGTGA | No |
| HUA0003-09 (SEQ ID NO: 19) | AACACCACACTCACC | 15 | SEQ ID NO: 50 | GGTGAGTGTGGTGTT | No |
| HUA0003-10 (SEQ ID NO: 20) | TACTAAGAGGAACAC | 15 | SEQ ID NO: 51 | GTGTTCCTCTTAGTA | Yes |
| HUA0003-11 (SEQ ID NO: 21) | AATGTATTAGTACTA | 15 | SEQ ID NO: 52 | TAGTACTAATACATT | No |
| HUA0003-12 (SEQ ID NO: 22) | TTACTGACTTAATGT | 15 | SEQ ID NO: 53 | ACATTAAGTCAGTAA | No |
| HUA0003-13 (SEQ ID NO: 23) | AAAGACTGACTTACT | 15 | SEQ ID NO: 54 | AGTAAGTCAGTCTTT | No |
| HUA0003-14 (SEQ ID NO: 24) | TTTAAATAAAAAAGA | 15 | SEQ ID NO: 55 | TCTTTTTTATTTAAA | No |
| HUA0003-15 (SEQ ID NO: 25) | AAAGGTTTTATTTAA | 15 | SEQ ID NO: 56 | TTAAATAAAACCTTT | No |
| HUA0003-0825 (SEQ ID NO: 26) | GTACTAAGAGGAACACCA | 18 | SEQ ID NO: 57 | TGGTGTTCCTCTTAGTAC | Yes |
| HUA0003-0926 (SEQ ID NO: 27) | AGTACTAAGAGGAACACC | 18 | SEQ ID NO: 58 | GGTGTTCCTCTTAGTACT | Yes |
| HUA0003-1027 (SEQ ID NO: 2) | TAGTACTAAGAGGAACAC | 18 | SEQ ID NO: 59 | GTGTTCCTCTTAGTACTA | Yes |
| HUA0003-1128 (SEQ ID NO: 28) | TTAGTACTAAGAGGAACA | 18 | SEQ ID NO: 60 | TGTTCCTCTTAGTACTAA | No |
| HUA0003-1229 (SEQ ID NO: 29) | ATTAGTACTAAGAGGAAC | 18 | SEQ ID NO: 61 | GTTCCTCTTAGTACTAAT | No |
| HUA0003-1330 (SEQ ID NO: 30) | TATTAGTACTAAGAGGAA | 18 | SEQ ID NO: 62 | TTCCTCTTAGTACTAATA | No |
| HUA0003-1431 (SEQ ID NO: 31) | GTATTAGTACTAAGAGGA | 18 | SEQ ID NO: 63 | TCCTCTTAGTACTAATAC | No |
| HUA0003-1532 (SEQ ID NO: 32) | TGTATTAGTACTAAGAGG | 18 | SEQ ID NO: 64 | CCTCTTAGTACTAATACA | No |
| HUA0003-1633 (SEQ ID NO: 33) | ATGTATTAGTACTAAGAG | 18 | SEQ ID NO: 65 | CTCTTAGTACTAATACAT | No |
| HUA0003-1734 (SEQ ID NO: 34) | AATGTATTAGTACTAAGA | 18 | SEQ ID NO: 66 | TCTTAGTACTAATACATT | No |

TABLE 1-continued

| ASO name | Sequence (5' to 3') | nt | Target Sequence name | Target (5' to 3') | >58% |
|---|---|---|---|---|---|
| HUA0003-1835 (SEQ ID NO: 35) | TAATGTATTAGTACTAAG | 18 | SEQ ID NO: 67 | CTTAGTACTAATACATTA | No |
| HUA0003-1936 (SEQ ID NO: 36) | TTAATGTATTAGTACTAA | 18 | SEQ ID NO: 68 | TTAGTACTAATACATTAA | No |
| HUA0003-0827 (SEQ ID NO: 37) | TAGTACTAAGAGGAACACCA | 20 | SEQ ID NO: 69 | TGGTGTTCCTCTTAGTACTA | Yes |
| HUA0003-0928 (SEQ ID NO: 9) | TTAGTACTAAGAGGAACACC | 20 | SEQ ID NO: 70 | GGTGTTCCTCTTAGTACTAA | Yes |
| HUA0003-1029 (SEQ ID NO: 3) | ATTAGTACTAAGAGGAACAC | 20 | SEQ ID NO: 71 | GTGTTCCTCTTAGTACTAAT | Yes |
| HUA0003-1130 (SEQ ID NO: 38) | TATTAGTACTAAGAGGAACA | 20 | SEQ ID NO: 72 | TGTTCCTCTTAGTACTAATA | Yes |
| HUA0003-1231 (SEQ ID NO: 39) | GTATTAGTACTAAGAGGAAC | 20 | SEQ ID NO: 73 | GTTCCTCTTAGTACTAATAC | Yes |
| HUA0003-0929 (SEQ ID NO: 8) | ATTAGTACTAAGAGGAACACC | 21 | SEQ ID NO: 74 | GGTGTTCCTCTTAGTACTAAT | Yes |
| HUA0003-1030 (SEQ ID NO: 4) | TATTAGTACTAAGAGGAACAC | 21 | SEQ ID NO: 75 | GTGTTCCTCTTAGTACTAATA | Yes |
| HUA0003-0930 (SEQ ID NO: 7) | TATTAGTACTAAGAGGAACACC | 22 | SEQ ID NO: 76 | GGTGTTCCTCTTAGTACTAATA | Yes |
| HUA0003-1031 (SEQ ID NO: 5) | GTATTAGTACTAAGAGGAACAC | 22 | SEQ ID NO: 77 | GTGTTCCTCTTAGTACTAATAC | Yes |
| HUA0003-0931 (SEQ ID NO: 10) | GTATTAGTACTAAGAGGAACACC | 23 | SEQ ID NO: 78 | GGTGTTCCTCTTAGTACTAATAC | Yes |
| HUA0003-1032 (SEQ ID NO: 6) | TGTATTAGTACTAAGAGGAACAC | 23 | SEQ ID NO: 79 | GTGTTCCTCTTAGTACTAATACA | Yes |

HEK293 cells were co-transfected with each ASO (10 nM) and the SLC26A4 minigene mutant. Exon 8 inclusion in untreated cells is ~30%. Exon 8 inclusion in cells treated with 10 nM control ASO (5'-UUCUCCGAACGUGUCACGUTT-3' (SEQ ID NO:80)) is ~26%. A number of ASOs potently promoted exon 8 inclusion. >58% incl: exon 8 inclusion was above 58% after treatment of 10 nM ASO.

TABLE 2

| Priority | Name | Sequence (5'-3') | Length (nt) |
|---|---|---|---|
| Group 1 | HUA0003-1027 (SEQ ID NO: 2) | TAGTACTAAGAGGAACAC | 18 |
| Group 1 | HUA0003-1029 (SEQ ID NO: 3) | ATTAGTACTAAGAGGAACAC | 20 |
| Group 1 | HUA0003-1030 (SEQ ID NO: 4) | TATTAGTACTAAGAGGAACAC | 21 |
| Group 2 | HUA0003-1031 (SEQ ID NO: 5) | GTATTAGTACTAAGAGGAACAC | 22 |
| Group 2 | HUA0003-1032 (SEQ ID NO: 6) | TGTATTAGTACTAAGAGGAACAC | 23 |

TABLE 2-continued

| Priority | Name | Sequence (5'-3') | Length (nt) |
|---|---|---|---|
| Group 2 | HUA0003-0930 (SEQ ID NO: 7) | TATTAGTAC TAAGAGGAA CACC | 22 |
| Group 2 | HUA0003-0929 (SEQ ID NO: 8) | ATTAGTACT AAGAGGAAC ACC | 21 |
| Group 2 | HUA0003-0928 (SEQ ID NO: 9) | TTAGTACTA AGAGGAACA CC | 20 |
| Group 2 | HUA0003-0931 (SEQ ID NO: 10) | GTATTAGTA CTAAGAGGA ACACC | 23 |
| Group 3 | HUA0003-10 (SEQ ID NO: 20) | TACTAAGAG GAACAC | 15 |
| Group 3 | HUA0003-0926 (SEQ ID NO: 27) | AGTACTAAG AGGAACACC | 18 |
| Group 3 | HUA0003-0825 (SEQ ID NO: 26) | GTACTAAGA GGAACACCA | 18 |
| Group 3 | HUA0003-0827 (SEQ ID NO: 37) | TAGTACTAA GAGGAACAC CA | 20 |
| Group 3 | HUA0003-1130 (SEQ ID NO: 38) | TATTAGTAC TAAGAGGAA CA | 20 |
| Group 3 | HUA0003-1231 (SEQ ID NO: 39) | GTATTAGTA CTAAGAGGA AC | 20 |

ASOs were listed in three groups from the most potent one to the weakest one in terms of their ability to correct exon 8 splicing of the SLC26A4 c.919-2A>G mutant.

FIG. 1 shows the exon 8 inclusion efficiencies of test ASOs. The percentage of exon 8 inclusion in untreated cells (Blank) is about 30%. The exon 8 inclusion percentage for negative control-treated ASO (Con ASO) is about 26%. While the test ASOs are all directed to the same 25-nt sequence in intron 8, they have varied degreed of exon 8 inclusion efficacies.

For example, HUA0003-1027 (SEQ ID NO:2), HUA0003-1029 (SEQ ID NO:3), and HUA0003-1030 (SEQ ID NO:4) reached exon 8 inclusion percentages of almost 90% inclusion. However, HUA0003-1231 (SEQ ID NO:39) only reached 58% exon 8 inclusion. This difference in efficacy is particularly remarkable since HUA0003-1029 (SEQ ID NO:3) and HUA0003-1231 (SEQ ID NO:39) are both 20 nucleotides long and are only shifted by two nucleotides.

TABLE 3

| 25-Nt Sequence of Interest: | 5'-tggtgttcctctt agtactaataca-3' | (SEQ ID NO: 41) |
|---|---|---|
| Reverse Complementary Seq: | 5'-tgtattagtacta agaggaacacca-3' | (SEQ ID NO: 1) |

TABLE 3-continued

| HUA0003-1027 (88% inclusion): | tagtactaagaggaac ac | (SEQ ID NO: 2) |
|---|---|---|
| HUA0003-1029 (88% inclusion): | attagtactaagagga acac | (SEQ ID NO: 3) |
| HUA0003-1030 (89% inclusion:) | tattagtactaagagga acac | (SEQ ID NO: 4) |
| HUA0003-1031 (83% inclusion): | gtattagtactaagagg aacac | (SEQ ID NO: 5) |
| HUA0003-1032 (83% inclusion): | tgtattagtactaag aggaacac | (SEQ ID NO: 6) |
| HUA0003-0930 (85% inclusion): | tattagtactaagagga acacc | (SEQ ID NO: 7) |
| HUA0003-0929 (82% inclusion): | attagtactaagaggaa cacc | (SEQ ID NO: 8) |
| HUA0003-0928 (82% inclusion): | ttagtactaagaggaac acc | (SEQ ID NO: 9) |
| HUA0003-0931 (77% inclusion): | gtattagtactaagagg aacacc | (SEQ ID NO: 10) |
| CONSERVED SEQ. (SEQ ID NO: 2): | [tagtactaagag gaacac] | |

Table 3 shows the ASOs that promote exon 8 inclusion, including their 5'-3' sequence and their exon 8 inclusion percentage. Table 3 also shows the relationship between the test ASOs and the conserved sequence they all share, which happens to be the same as SEQ ID NO:2.

Figure 2:
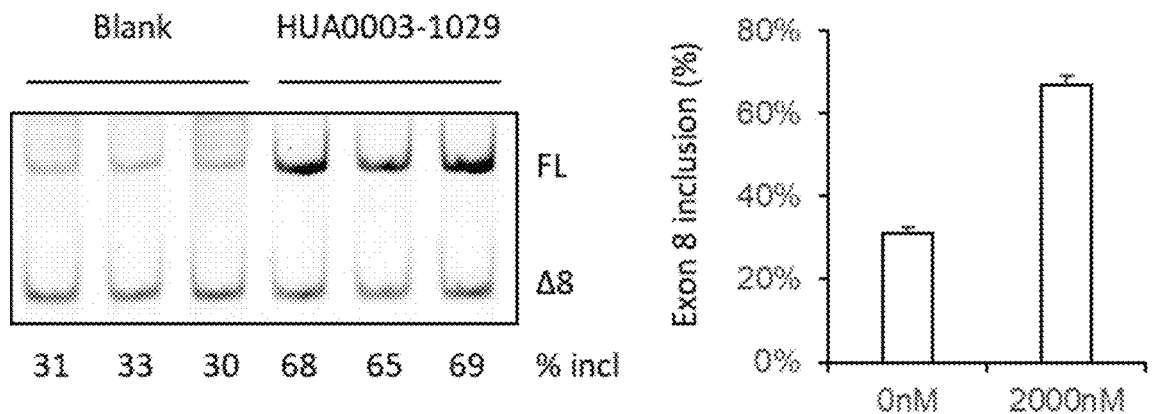
FIG. 2 shows exon 8 inclusion of endogenous SLC26A4 c.919-2A>G mutant in PBMC's derived from a patient using ASO (SEQ ID NO:3). PBMC: peripheral blood mononuclear cell, FL: full-length transcript, Δ8: exon 8-skipped transcript.
Figure 3:
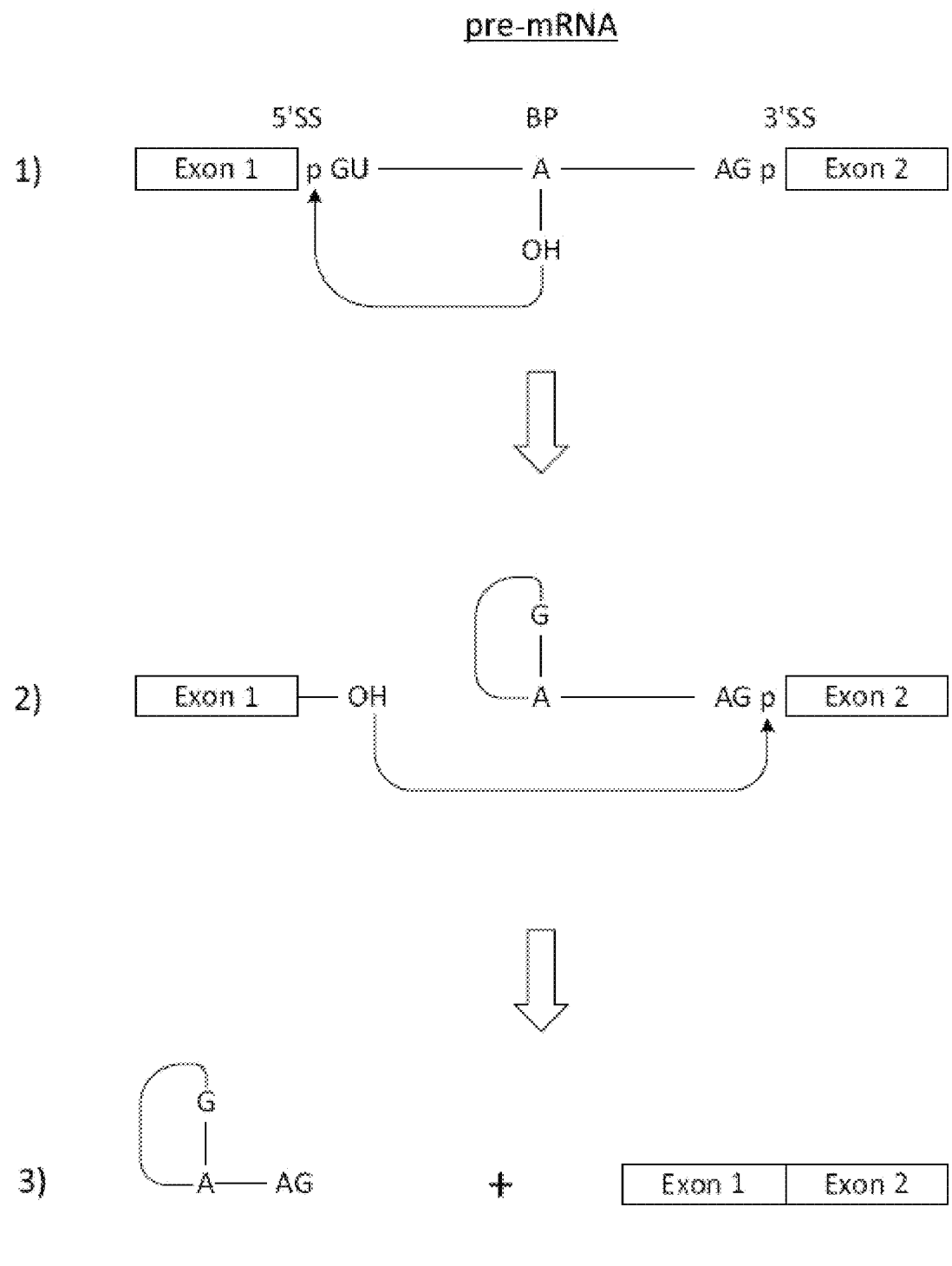
FIG. 3 shows the two transesterification reactions involved in splicing pre-mRNA. The 2' OH group of the branch site binds to the 5' splice site via a nucleophilic attack, causing cleavage of the 5' exon and forming a lariat between the 5' splice site and the branch site. Then the 3' OH group of the 5' exon binds to the 3' exon at the 3' splice site, cleaving the intron lariat and ligating the exons to from mRNA. 5'SS: 5' splice site; 3'SS: 3' splice site; BS: branch site.

FIG. 2 shows the promotion of exon 8 inclusion of endogenous SLC26A4 c.919-2A>G in peripheral blood mononuclear cells (PBMCs) derived from a patient. PBMCs were isolated from a c.919-2A>G homozygous patient by density gradient centrifugation, then cells were cultured in (Rosewell Park Memorial Institute (RPMI) 1640 complete medium (Invitrogen). Cholesterol-conjugated ASO (dissolved in water) was added to $10^6$ cells per well in a 12-well plate with low-serum (3% FBS) complete medium. The final concentration of ASO was 2 μM. After 48 h, cells were collected for RNA purification and splicing analysis.

Those having ordinary skill in the art will appreciate that the disclosed invention can be modified in ways not specifically described herein. The disclosed invention is not to be limited in scope by the specific embodiments described herein, which are for illustrative purposes only. The invention includes any modifications and variations, including all functionally equivalent productions, compositions, and methods.

The entire disclosures of all publications cited herein are hereby incorporated by reference. No admission is made that any such publication constitutes prior art or is part of the common general knowledge of those having ordinary skill in the art.

What is claimed is:

1. A chemically modified antisense oligonucleotide of 10-30 nucleotides in length comprising all or a portion of SEQ ID NO:1 (5'-tgtattagtactaagaggaacacca-3'), wherein the antisense oligonucleotide is:

a. HUA0003-1027

(SEQ ID NO: 2)
(5'-tagtactaagaggaacac-3');

b. HUA0003-1029

(SEQ ID NO: 3)
(5'-attagtactaagaggaacac-3');

c. HUA0003-1030

(SEQ ID NO: 4)
(5'-tattagtactaagaggaacac-3');

d. HUA0003-1031

(SEQ ID NO: 5)
(5'-gtattagtactaagaggaacac-3');

-continued

```
e. HUA0003-1032
                                    (SEQ ID NO: 6)
   (5'-tgtattagtactaagaggaacac-3');
f. HUA0003-0930
                                    (SEQ ID NO: 7)
   (5'-tattagtactaagaggaacacc-3');
g. HUA0003-0929
                                    (SEQ ID NO: 8)
   (5'-attagtactaagaggaacacc-3');
h. HUA0003-0928
                                    (SEQ ID NO: 9)
   (5'-ttagtactaagaggaacacc-3');
or
i. HUA0003-0931
                                   (SEQ ID NO: 10)
   (5'-gtattagtactaagaggaacacc-3').
```

2. The antisense oligonucleotide of claim 1, wherein the antisense oligonucleotide comprises a non-natural backbone.

3. The antisense oligonucleotide of claim 2, wherein the non-natural backbone comprises modified sugar moieties.

4. The antisense oligonucleotide of claim 3, wherein the modified sugar moieties comprise 2'-O-methoxyethyl ribose.

5. The antisense oligonucleotide of claim 2, wherein the non-natural backbone comprises modified phosphates.

6. The antisense oligonucleotide of claim 5, wherein the modified phosphates comprise phosphorothioates.

7. The antisense oligonucleotide of claim 1, wherein the antisense oligonucleotide comprises modified nitrogenous bases.

8. The antisense oligonucleotide of claim 7, wherein the modified nitrogenous bases comprise 5-methylcytosine bases.

9. The antisense oligonucleotide of claim 1 further comprising a pharmaceutically acceptable carrier or excipient.

10. A method of preventing or reducing exon 8 skipping in the SLC26A4 gene during pre-mRNA splicing, comprising introducing a nucleic acid molecule into a cell, wherein the nucleic acid molecule is an antisense oligonucleotide comprising all or a portion of SEQ ID NO:1 (5'-tgtattagtactaagaggaacacca-3'), wherein the oligonucleotide hybridizes to an intron 8 target region of the SLC26A4 gene, and wherein the oligonucleotide prevents or reduces exon 8 skipping during pre-mRNA splicing of the SLC26A4 gene.

11. The method of claim 10, wherein the antisense oligonucleotide is:

```
a. HUA0003-1027
                                    (SEQ ID NO: 2)
   (5'-tagtactaagaggaacac-3');
b. HUA0003-1029
                                    (SEQ ID NO: 3)
   (5'-attagtactaagaggaacac-3');
c. HUA0003-1030
                                    (SEQ ID NO: 4)
   (5'-tattagtactaagaggaacac-3');
d. HUA0003-1031
                                    (SEQ ID NO: 5)
   (5'-gtattagtactaagaggaacac-3');
e. HUA0003-1032
                                    (SEQ ID NO: 6)
   (5'-tgtattagtactaagaggaacac-3');
f. HUA0003-0930
                                    (SEQ ID NO: 7)
   (5'-tattagtactaagaggaacacc-3');
g. HUA0003-0929
                                    (SEQ ID NO: 8)
   (5'-attagtactaagaggaacacc-3');
h. HUA0003-0928
                                    (SEQ ID NO: 9)
   (5'-ttagtactaagaggaacacc-3');
or
i. HUA0003-0931
                                   (SEQ ID NO: 10)
   (5'-gtattagtactaagaggaacacc-3').
```

12. The method of claim 10, wherein the cell is an animal cell.

13. The method of claim 12, wherein the cell is a human cell.

14. The method of claim 10, wherein the nucleic acid molecule is introduced into a cell by way of an expression vector.

15. The method of claim 14, wherein the expression vector is a pCI-neo expression vector.

16. A method of treating hearing loss in a subject in a subject having Pendred syndrome comprising administering a therapeutically effective amount of the antisense oligonucleotide of claim 1.

17. The method of claim 16, wherein the antisense oligonucleotide is administered via parenteral administration.

\* \* \* \* \*

SEQUENCE LISTING

<160> NUMBER OF SEQ ID NOS: 80

<210> SEQ ID NO 1
<211> LENGTH: 25
<212> TYPE: DNA
<213> ORGANISM: Homo sapiens

<400> SEQUENCE: 1
tgtattagta ctaagaggaa cacca                                          25

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tagtactaag aggaacac                                                  18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
attagtacta agaggaacac                                                20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tattagtact aagaggaaca c                                              21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtattagtac taagaggaac ac                                             22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgtattagta ctaagaggaa cac                                            23

<210> SEQ ID NO 7

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tattagtact aagaggaaca cc                                              22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
attagtacta agaggaacac c                                               21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttagtactaa gaggaacacc                                                 20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtattagtac taagaggaac acc                                             23

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcagtagcaa ttatc                                                      15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atatgaaatg gcagt                                                      15

<210> SEQ ID NO 13
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggttggctcc atatg                                                      15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tttttttcca ggttg                                                      15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcattgtaa ttttt                                                      15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
taacaatgcc agcat                                                      15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggatggatt taaca                                                      15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcaccccctt gggat                                                      15

<210> SEQ ID NO 19
<211> LENGTH: 15
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 19
aacaccacac tcacc                                                    15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tactaagagg aacac                                                    15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatgtattag tacta                                                    15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttactgactt aatgt                                                    15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaagactgac ttact                                                    15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tttaaataaa aaaga                                                    15

<210> SEQ ID NO 25
<211> LENGTH: 15
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 25 aaaggttttta tttaa                                                       15

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtactaagag gaacacca                                                     18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agtactaaga ggaacacc                                                     18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttagtactaa gaggaaca                                                     18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
attagtacta agaggaac                                                     18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tattagtact aagaggaa                                                     18

<210> SEQ ID NO 31
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 31
gtattagtac taagagga                                                 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgtattagta ctaagagg                                                 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgtattagt actaagag                                                 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aatgtattag tactaaga                                                 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
taatgtatta gtactaag                                                 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttaatgtatt agtactaa                                                 18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
tagtactaag aggaacacca                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tattagtact aagaggaaca                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtattagtac taagaggaac                                               20

<210> SEQ ID NO 40
<211> LENGTH: 271
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gtaagtagaa tatgtagtta gaaagttcag cattatttgg ttgacaaaca aggaattatt    60
aaaaccaatg gagtttttaa catcttttgt tttatttcgg acgataattg ctactgccat   120
ttcatatgga gccaacctgg aaaaaaatta caatgctggc attgttaaat ccatcccaag   180
ggggtgagtg tggtgttcct cttagtacta atacattaag tcagtaagtc agtctttttt   240
atttaaataa aacctttttat tacaagcttc a                                 271

<210> SEQ ID NO 41
<211> LENGTH: 25
<212> TYPE: DNA
<213> ORGANISM: Homo sapiens

<400> SEQUENCE: 41
tggtgttcct cttagtacta ataca                                         25

<210> SEQ ID NO 42
<211> LENGTH: 15
<212> TYPE: DNA
<213> ORGANISM: Homo sapiens

<400> SEQUENCE: 42
gataattgct actgc                                                    15

<210> SEQ ID NO 43
<211> LENGTH: 15
<212> TYPE: DNA
<213> ORGANISM: Homo sapiens

```
<400> SEQUENCE: 43
actgccattt catat                                                    15

<210> SEQ ID NO 44
<211> LENGTH: 15
<212> TYPE: DNA
<213> ORGANISM: Homo sapiens

<400> SEQUENCE: 44
catatggagc caacc                                                    15

<210> SEQ ID NO 45
<211> LENGTH: 15
<212> TYPE: DNA
<213> ORGANISM: Homo sapiens

<400> SEQUENCE: 45
caacctggaa aaaaa                                                    15

<210> SEQ ID NO 46
<211> LENGTH: 15
<212> TYPE: DNA
<213> ORGANISM: Homo sapiens

<400> SEQUENCE: 46
aaaaattaca atgct                                                    15

<210> SEQ ID NO 47
<211> LENGTH: 15
<212> TYPE: DNA
<213> ORGANISM: Homo sapiens

<400> SEQUENCE: 47
atgctggcat tgtta                                                    15

<210> SEQ ID NO 48
<211> LENGTH: 15
<212> TYPE: DNA
<213> ORGANISM: Homo sapiens

<400> SEQUENCE: 48
tgttaaatcc atccc                                                    15

<210> SEQ ID NO 49
<211> LENGTH: 15
<212> TYPE: DNA
<213> ORGANISM: Homo sapiens

<400> SEQUENCE: 49
atcccaaggg ggtga                                                    15

<210> SEQ ID NO 50
<211> LENGTH: 15
<212> TYPE: DNA
<213> ORGANISM: Homo sapiens

<400> SEQUENCE: 50
ggtgagtgtg gtgtt                                                    15

<210> SEQ ID NO 51
<211> LENGTH: 15
<212> TYPE: DNA
```

```
<400> SEQUENCE: 51
gtgttcctct tagta                                              15

<210> SEQ ID NO 52
<211> LENGTH: 15
<212> TYPE: DNA
<213> ORGANISM: Homo sapiens

<400> SEQUENCE: 52
tagtactaat acatt                                              15

<210> SEQ ID NO 53
<211> LENGTH: 15
<212> TYPE: DNA
<213> ORGANISM: Homo sapiens

<400> SEQUENCE: 53
acattaagtc agtaa                                              15

<210> SEQ ID NO 54
<211> LENGTH: 15
<212> TYPE: DNA
<213> ORGANISM: Homo sapiens

<400> SEQUENCE: 54
agtaagtcag tcttt                                              15

<210> SEQ ID NO 55
<211> LENGTH: 15
<212> TYPE: DNA
<213> ORGANISM: Homo sapiens

<400> SEQUENCE: 55 tctttttat ttaaa                                               15

<210> SEQ ID NO 56
<211> LENGTH: 15
<212> TYPE: DNA
<213> ORGANISM: Homo sapiens

<400> SEQUENCE: 56
ttaaataaaa ccttt                                              15

<210> SEQ ID NO 57
<211> LENGTH: 18
<212> TYPE: DNA
<213> ORGANISM: Homo sapiens

<400> SEQUENCE: 57
tggtgttcct cttagtac                                           18

<210> SEQ ID NO 58
<211> LENGTH: 18
<212> TYPE: DNA
<213> ORGANISM: Homo sapiens

<400> SEQUENCE: 58
ggtgttcctc ttagtact                                           18

<210> SEQ ID NO 59
<211> LENGTH: 18
<212> TYPE: DNA
```

```
<213> ORGANISM: Homo sapiens

<400> SEQUENCE: 59
gtgttcctct tagtacta                                                 18

<210> SEQ ID NO 60
<211> LENGTH: 18
<212> TYPE: DNA
<213> ORGANISM: Homo sapiens

<400> SEQUENCE: 60
tgttcctctt agtactaa                                                 18

<210> SEQ ID NO 61
<211> LENGTH: 18
<212> TYPE: DNA
<213> ORGANISM: Homo sapiens

<400> SEQUENCE: 61
gttcctctta gtactaat                                                 18

<210> SEQ ID NO 62
<211> LENGTH: 18
<212> TYPE: DNA
<213> ORGANISM: Homo sapiens

<400> SEQUENCE: 62
ttcctcttag tactaata                                                 18

<210> SEQ ID NO 63
<211> LENGTH: 18
<212> TYPE: DNA
<213> ORGANISM: Homo sapiens

<400> SEQUENCE: 63
tcctcttagt actaatac                                                 18

<210> SEQ ID NO 64
<211> LENGTH: 18
<212> TYPE: DNA
<213> ORGANISM: Homo sapiens

<400> SEQUENCE: 64
cctcttagta ctaataca                                                 18

<210> SEQ ID NO 65
<211> LENGTH: 18
<212> TYPE: DNA
<213> ORGANISM: Homo sapiens

<400> SEQUENCE: 65
ctcttagtac taatacat                                                 18

<210> SEQ ID NO 66
<211> LENGTH: 18
<212> TYPE: DNA
<213> ORGANISM: Homo sapiens

<400> SEQUENCE: 66
tcttagtact aatacatt                                                 18

<210> SEQ ID NO 67
<211> LENGTH: 18
```

```
<212> TYPE: DNA
<213> ORGANISM: Homo sapiens

<400> SEQUENCE: 67
cttagtacta atacatta                                                   18

<210> SEQ ID NO 68
<211> LENGTH: 18
<212> TYPE: DNA
<213> ORGANISM: Homo sapiens

<400> SEQUENCE: 68
ttagtactaa tacattaa                                                   18

<210> SEQ ID NO 69
<211> LENGTH: 20
<212> TYPE: DNA
<213> ORGANISM: Homo sapiens

<400> SEQUENCE: 69
tggtgttcct cttagtacta                                                 20

<210> SEQ ID NO 70
<211> LENGTH: 20
<212> TYPE: DNA
<213> ORGANISM: Homo sapiens

<400> SEQUENCE: 70
ggtgttcctc ttagtactaa                                                 20

<210> SEQ ID NO 71
<211> LENGTH: 20
<212> TYPE: DNA
<213> ORGANISM: Homo sapiens

<400> SEQUENCE: 71
gtgttcctct tagtactaat                                                 20

<210> SEQ ID NO 72
<211> LENGTH: 20
<212> TYPE: DNA
<213> ORGANISM: Homo sapiens

<400> SEQUENCE: 72
tgttcctctt agtactaata                                                 20

<210> SEQ ID NO 73
<211> LENGTH: 20
<212> TYPE: DNA
<213> ORGANISM: Homo sapiens

<400> SEQUENCE: 73
gttcctctta gtactaatac                                                 20

<210> SEQ ID NO 74
<211> LENGTH: 21
<212> TYPE: DNA
<213> ORGANISM: Homo sapiens

<400> SEQUENCE: 74
ggtgttcctc ttagtactaa t                                               21

<210> SEQ ID NO 75
```

```
<211> LENGTH: 21
<212> TYPE: DNA
<213> ORGANISM: Homo sapiens

<400> SEQUENCE: 75
gtgttcctct tagtactaat a                                              21

<210> SEQ ID NO 76
<211> LENGTH: 22
<212> TYPE: DNA
<213> ORGANISM: Homo sapiens

<400> SEQUENCE: 76
ggtgttcctc ttagtactaa ta                                             22

<210> SEQ ID NO 77
<211> LENGTH: 22
<212> TYPE: DNA
<213> ORGANISM: Homo sapiens

<400> SEQUENCE: 77
gtgttcctct tagtactaat ac                                             22

<210> SEQ ID NO 78
<211> LENGTH: 23
<212> TYPE: DNA
<213> ORGANISM: Homo sapiens

<400> SEQUENCE: 78
ggtgttcctc ttagtactaa tac                                            23

<210> SEQ ID NO 79
<211> LENGTH: 23
<212> TYPE: DNA
<213> ORGANISM: Homo sapiens

<400> SEQUENCE: 79
gtgttcctct tagtactaat aca                                            23

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
uucuccgaac gugucacgut t                                              21
```